(12) United States Patent
Hsiao

(10) Patent No.: US 10,596,293 B2
(45) Date of Patent: Mar. 24, 2020

(54) SCENT AIR PURIFIER CAPABLE OF REPLACING CASE THEREOF

(71) Applicant: DONGGUAN YIH TEH ELECTRIC PRODUCTS CO., LTD.

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 38 days.

(21) Appl. No.: 15/985,501

(22) Filed: May 21, 2018

(65) Prior Publication Data
US 2019/0247532 A1   Aug. 15, 2019

Related U.S. Application Data

(63) Continuation-in-part of application No. 15/893,962, filed on Feb. 12, 2018.

(51) Int. Cl.
| | |
|---|---|
| *A61L 9/12* | (2006.01) |
| *B01F 3/04* | (2006.01) |
| *B01D 35/30* | (2006.01) |
| *B01D 46/24* | (2006.01) |
| *A61L 9/14* | (2006.01) |
| *A61L 9/03* | (2006.01) |
| *B01D 46/00* | (2006.01) |

(52) U.S. Cl.
CPC ............... *A61L 9/122* (2013.01); *A61L 9/032* (2013.01); *A61L 9/14* (2013.01); *B01D 35/30* (2013.01); *B01D 46/24* (2013.01); *B01F 3/04* (2013.01); *A61L 2209/111* (2013.01); *A61L 2209/133* (2013.01); *B01D 46/0002* (2013.01)

(58) Field of Classification Search
CPC . B01F 3/04; B01D 46/24; B01D 35/30; F24F 1/02; A61L 9/127
USPC ............ 96/417, 222; 55/471; 239/53, 54, 55
See application file for complete search history.

(56) References Cited

U.S. PATENT DOCUMENTS

| | | |
|---|---|---|
| 7,963,460 B2 | 6/2011 | Hsiao |
| 7,992,801 B2 | 8/2011 | Hsiao |
| 8,029,153 B2 | 10/2011 | Hsiao |
| 8,133,440 B2 | 3/2012 | Hsiao |

(Continued)

FOREIGN PATENT DOCUMENTS

| | | | | |
|---|---|---|---|---|
| CN | 204534873 U | * | 8/2015 | ............... F24F 1/02 |
| CN | 205119264 U | * | 3/2016 | ............... F24F 1/02 |

*Primary Examiner* — Robert A Hopkins
(74) *Attorney, Agent, or Firm* — Sinorica, LLC

(57) ABSTRACT

A scent air purifier contains a body, a fan, a filter element, a holder, a circuit control unit, a case removable from the body. The body includes an accommodation chamber, a receiving groove, and a first vent. The accommodation chamber is defined in the body, the receiving groove is located above the accommodation chamber, and the first vent communicates with the accommodation chamber and the receiving groove. The fan is accommodated in the accommodation chamber. The filter element is connected below the accommodation chamber and communicates with air from an external environment outside the body so that the fan delivers the air to flow through the first vent and the receiving groove, after drawing the air from the external environment. The holder is connected with the body, and the circuit control unit is housed in the holder and is electrically connected with a power source and the fan.

18 Claims, 4 Drawing Sheets

(56) References Cited

U.S. PATENT DOCUMENTS

| | | |
|---|---|---|
| 8,196,903 B2 | 6/2012 | Hsiao |
| 9,022,365 B2 * | 5/2015 | Brosmith ............ B01F 3/04085 |
| | | 261/142 |
| 2015/0246309 A1 * | 9/2015 | Gruenbacher ......... B01D 46/42 |
| | | 96/417 |

* cited by examiner

SCENT AIR PURIFIER CAPABLE OF REPLACING CASE THEREOF

This application is a Continuation-in-Part of application Ser. No. 15/893,962, filed Feb. 12, 2018.

BACKGROUND OF THE INVENTION

Field of the Invention

The present invention relates to a scent diffuser, and more particularly to a scent air purifier capable of replacing a case of the scent air purifier.

Description of the Prior Art

A conventional scent diffuser is employed to diffuse fragrance smell or to eliminate odors, but it cannot filter and purify air.

A fragrance diffuser is disclosed in U.S. D620,574, but it cannot filter and purify air. A detachable aromatic nebulizing diffuser is disclosed in U.S. Pat. No. 7,963,460 and contains an ultrasonic oscillator configured to oscillate fluid so as to produce fragrance smell, and the fragrance smell is delivered by the fan so as to diffuse toward external environment, yet it cannot filter and purify air. A lamp-based scent releasing system is disclosed in U.S. Pat. No. 8,201,957 and contains a heater configured to heat aromatic substances, thus diffusing the fragrance smell. However, the heat aromatic substances cannot be replaceable quickly, and the lamp-based scent releasing system cannot filter and purify air.

The present invention has arisen to mitigate and/or obviate the afore-described disadvantages.

SUMMARY OF THE INVENTION

The primary aspect of the present invention is to provide a scent air purifier which filters air and diffuses fragrance smell.

Another aspect of the present invention is to provide a scent air purifier which diffuses the fragrance smell easily and safely.

To obtain the above aspect, a scent air purifier provided by the present invention contains: a body, a fan, a filter element, a holder, and a circuit control unit.

The body includes an accommodation chamber, a receiving groove, a first vent, wherein the accommodation chamber is defined in the body, the receiving groove is located above the accommodation chamber, and the first vent is formed between and communicates with the accommodation chamber and the receiving groove.

The fan is accommodated in the accommodation chamber.

The filter element is connected below the accommodation chamber of the body and communicates with air from an external environment outside the body so that the fan delivers the air to flow through the first vent and the receiving groove, after the fan draws the air from the external environment.

The holder is connected with a lower end of the body.

The circuit control unit is housed in the holder and is electrically connected with a power source and the fan.

The holder is connected with a lower end of the body and accommodates the circuit control unit, and the circuit control unit is electrically connected with a power source and the fan so as to supply a power to the fan. Accordingly, the fan delivers the air from the external environment, the filter element filters the air (in which dusts and particulate matters contain) so as to eliminate and purify PM 2.5 of the air, and the air flows to the external environment via the accommodation chamber, the fan, the first vent and the receiving groove.

The body further includes a first through orifice defined between an upper end of the accommodation camber and the receiving groove and communicating with the accommodation chamber, such that the fan delivers the air from the external environment via the filter element, wherein when a part of the air flows through the first vent and the receiving groove, the other part of the air flows to the first through orifice via the accommodation chamber of the body and the fan, thus cleaning and flowing the air to the external environment.

The scent air purifier further contains a scent diffusion unit in which aromatic substances are accommodated, and the scent diffusion unit is housed in the receiving groove of the body, the circuit control unit is electrically connected with the power source (not shown) so as to supply the power to the fan, by which the fan rotates and delivers the air to flow through the filter element from the external environment, such that the air flows into the receiving groove via the accommodation chamber, the fan, and the first vents after beings filtered and cleaned by the filter element so that the scent diffusion unit of the receiving groove is blown by the air, thus diffusing scents to the external environment directly via the second through orifice of the case. Preferably, the aromatic substances of the scent diffusion unit are any one of essential oil, volatile aromatic liquids, scented oils, scented essences, flower essences, perfumes, and aromatic agent.

The scent diffusion unit is a solid capsule which has the scent carrier, a shell, a lid, and multiple second vents. The shell has a mouth defined on a top thereof, and the multiple second vents are formed on a bottom of the shell. The scent carrier absorbs at least one of the aromatic substances and is housed in the shell, and the lid is covered on the mouth, wherein an adjustable spraying gap is defined between the lid and the mouth, the scent diffusion unit (i.e., the solid capsule) is accommodated in the receiving groove of the body, and the adjustable spraying gap of the solid capsule extends out of the second through orifice of the case. The control circuit unit is electrically connected with the power source (not shown) so as to supply the power to the fan, and the fan operates and delivers the air to be filtered by the filter element, the air is delivered into the solid capsule through the accommodation chamber of the body, the fan, the first vent, the receiving groove, and the multiple second vents, hence the air blows the scent carrier so as to diffuse the fragrance smell out of the scent air purifier via the second through orifice of the case. Accordingly, the scent air purifier is simplified, reduces power consumption, and operates safely.

The filter element contains a first filtration layer, a second filtration layer, and a third filtration layer. The first filtration layer is made of nanosilver so as to stop hairs, furs, dusts, debrides, and fluffs. The second layer is high-efficiency particulate air (HEPA) so as to attach dusts and PM 2.5. The third layer is an activated carbon filter so as to filter odors, smoke, and formaldehyde.

DETAILED DESCRIPTION OF THE PREFERRED EMBODIMENTS

Figure 1:
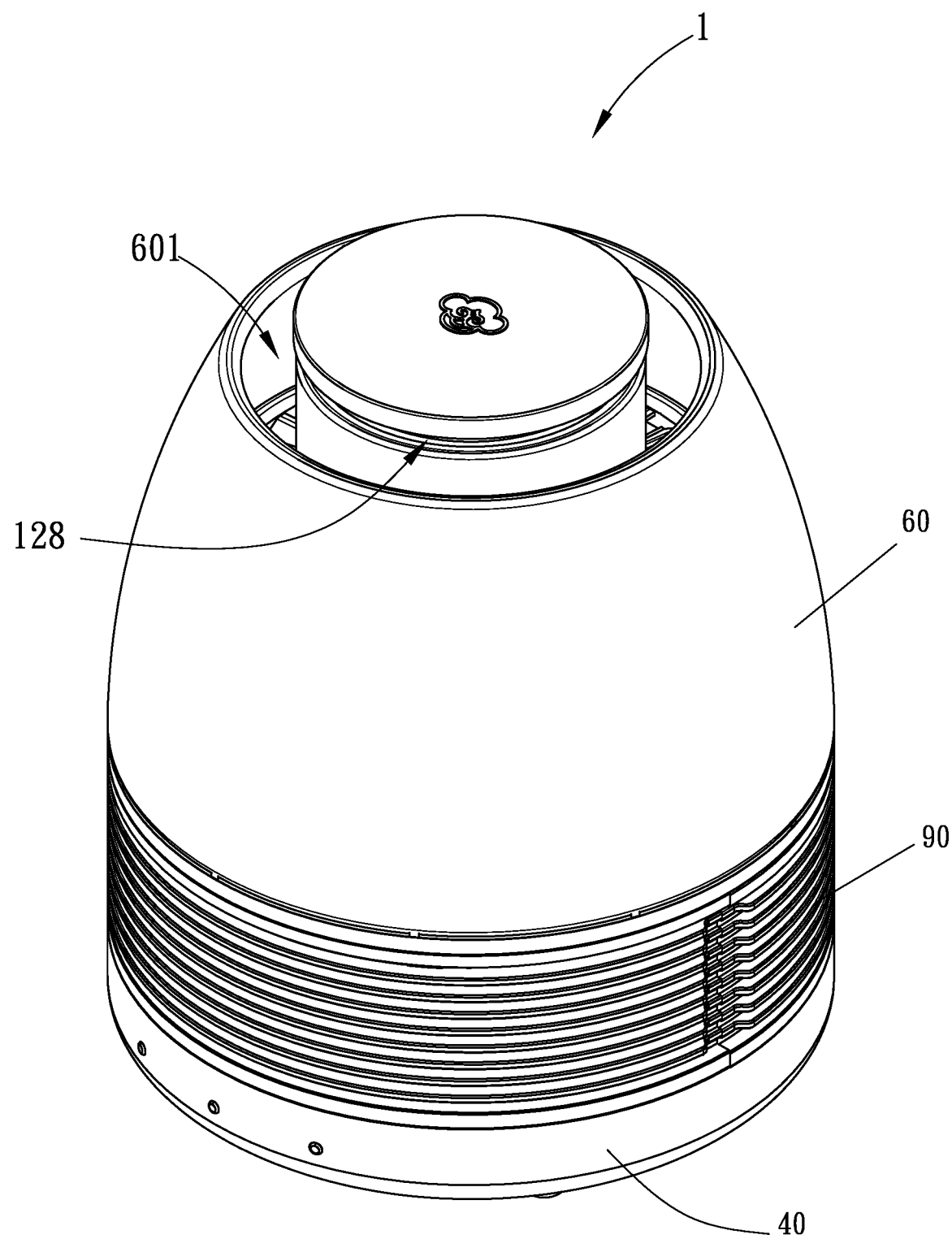
FIG. 1 is a perspective view showing the assembly of a scent air purifier according to a preferred embodiment of the present invention.

With reference to FIGS. 1-4, a scent air purifier 1 according to a preferred embodiment of the present invention comprises: a body 10, a fan 20, a filter element 30, a holder 40, and a circuit control unit 50.

The body 10 includes an accommodation chamber 11, a receiving groove 13, a first vent 15, wherein the accommodation chamber 11 is defined in the body 10, the receiving groove 13 is located above the accommodation chamber 11, and the first vent 15 is formed between and communicates with the accommodation chamber 11 and the receiving groove 13.

The fan 20 is accommodated in the accommodation chamber 11, and the filter element 30 is connected below the accommodation chamber 11 of the body 10 and communicates with air form an external environment outside the body 10. The fan 20 draws air from the external environment and delivers the air to flow through the first vent 15 and the accommodation chamber 13.

The holder 40 is connected with a lower end of the body 10 and accommodates the circuit control unit 50, and the circuit control unit 50 is electrically connected with a power source (not shown) and the fan 20 so as to supply a power to the fan 20. Accordingly, the fan 20 delivers the air from the external environment, the filter element 30 filters the air (in which dusts and particulate matters contain) so as to eliminate and purify PM 2.5 of the air, and the air flows to the external environment via the accommodation chamber 11, the fan 20, the first vent 15, and the receiving groove 13.

Figure 2:
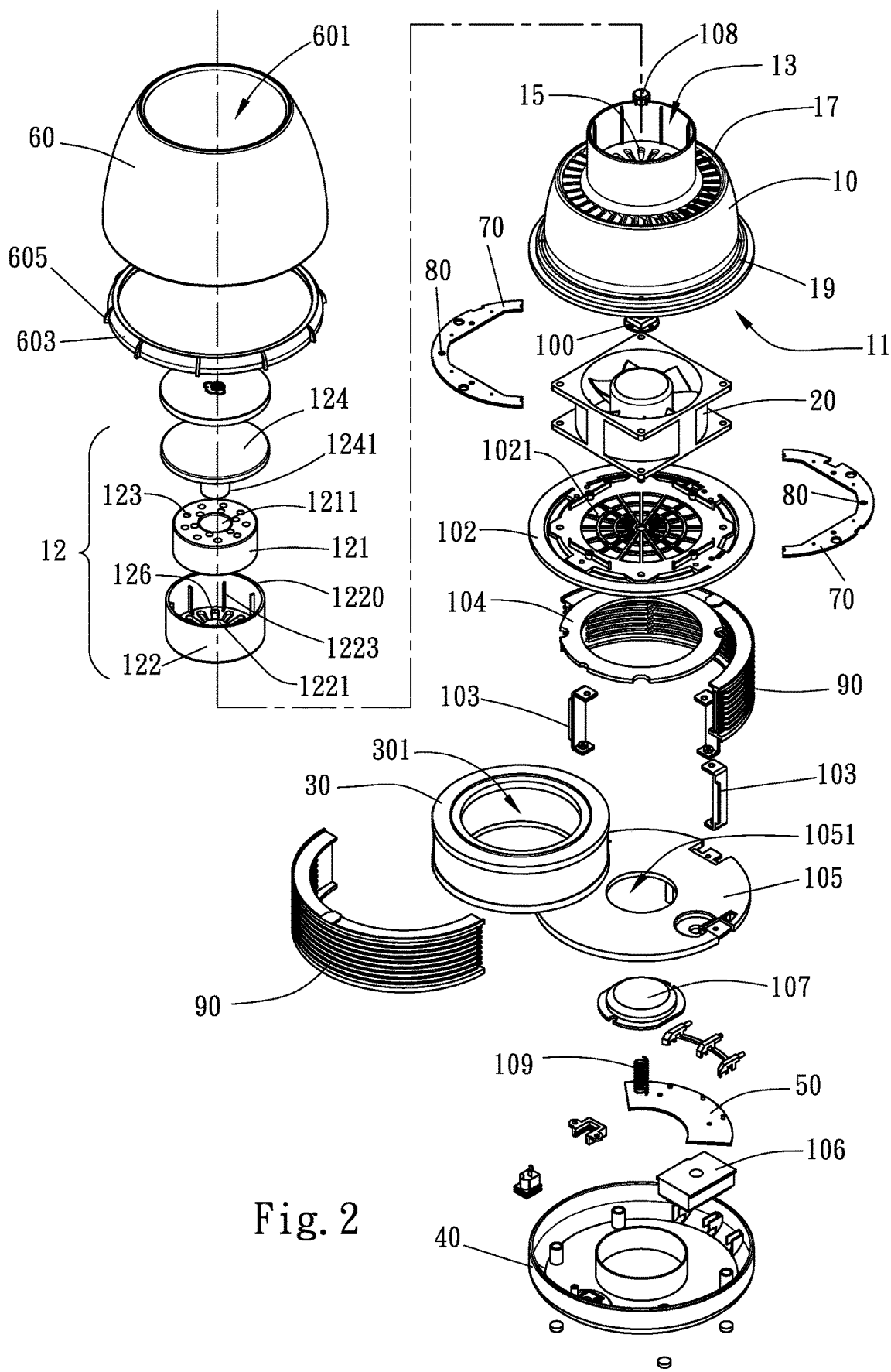
FIG. 2 is a perspective view showing the exploded components of the scent air purifier according to the preferred embodiment of the present invention.
Figure 4:
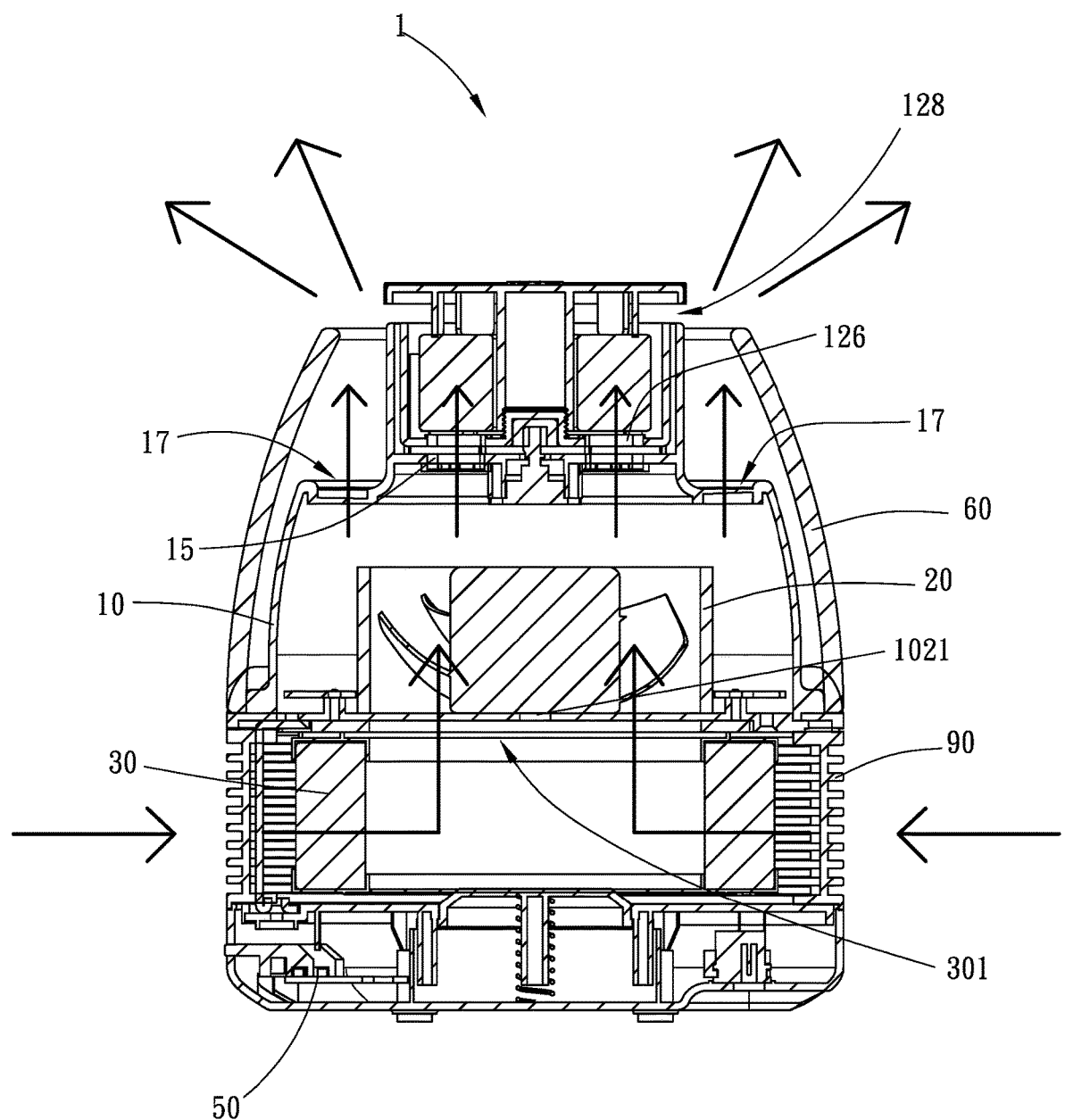
FIG. 4 is a cross sectional view showing the operation of the scent air purifier according to the preferred embodiment of the present invention.

Referring to FIGS. 2 and 4, the body 10 further includes a first through orifice 17 defined between an upper end of the accommodation camber 11 and the receiving groove 13 and communicating with the accommodation chamber 11, such that the fan 20 delivers the air from the external environment via the filter element 30, wherein when a part of the air flows through the first vent 15 and the receiving groove 13, the other part of the air flows to the first through orifice 17 via the accommodation chamber 11 of the body 10 and the fan 20, thus cleaning and flowing the air to the external environment.

Figure 3:
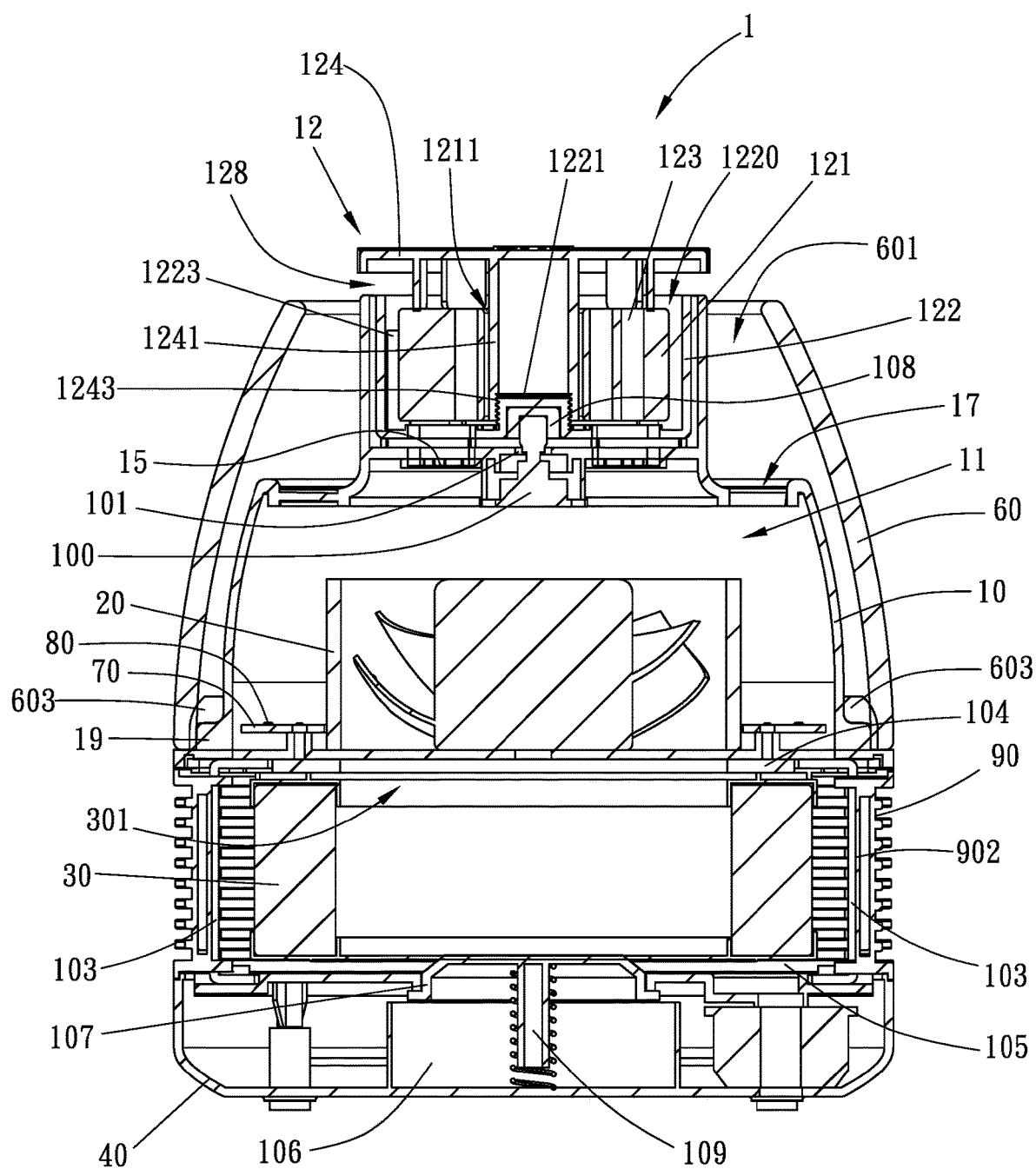
FIG. 3 is a cross sectional view showing the assembly of the scent air purifier according to the preferred embodiment of the present invention.

As shown in FIGS. 2-4, the scent air purifier 1 further comprises a case 60 which includes a second through orifice 601 formed on a side of the case 60, wherein the case 60 is hollow and is detachably retained with an outer wall of the body 10 so as to replace cases 60 of various types or patterns based on using requirements. The air is filtered by the filer element 30 and flows to the external environment from the receiving groove 13 or the first through orifice 17 via the second through orifice 601.

The body 10 further includes a stepped rib 19 extending outward from the outer wall of the body 10, wherein the case 60 is hollow, and when the case 60 covers on the outer wall of the body 10, an inner wall of the case 60 is detachably retained with the stepped rib 19 of the body 10.

As illustrated in FIGS. 2-4, the scent air purifier 1 further comprises a support loop 603 and multiple tabs 605 arranged around a peripheral side of the support loop 603. When the case 60 covers on the outer wall of the body 10, the inner wall of the case 60 is removably retained with the multiple tabs 605 of the support loop 603, wherein the multiple tabs 650 are flexible. When the case 60 covers on the outer wall of the body 10, the inner wall of the case 60 forces the multiple tabs 605 to flexibly deform so that the multiple tabs 605 urges the support loop 603 to abut against the body 10. Furthermore, the case 60 is removable from the body 10 so as to be replaced easily.

The support loop 603 is made of any one of rubber, silicone rubber, and plastic.

With reference to FIGS. 2 and 3, the filter element 30 is in a hollow column shape and includes a closed filtering structure formed on a bottom of the filter element 30. The filter element 30 includes an opening 301 defined on a top of the filter element 30 and connecting with a lower end of the accommodation chamber 11 of the body 10, such that the air is filtered by the filter element 30 from the fan 20 and flows into the accommodation chamber 11, the first vent 15, and the receiving groove 13 from the opening 301.

The scent air purifier 1 further comprises multiple cleaning meshes 90 arranged around an outer wall of the filter element 30 and located between the body 10 and the holder 40 so as to filter the dusts and to attach hairs and furs.

Referring to FIGS. 2-4, the scent air purifier 1 further comprises multiple fixing elements 103, and each of the multiple cleaning meshes 90 includes a housing trench 902 defined inside an outer wall of each cleaning mesh 90 and accommodating the multiple fixing elements 103, wherein two ends of each of the multiple fixing elements 103 fix the filter element 30.

As shown in FIGS. 2-3, the scent air purifier 1 further comprises multiple circuit boards 70, multiple light emitting elements 80 respectively arranged on the multiple circuit boards 70, wherein the multiple circuit boards 70 are electrically connected with the control circuit unit 50 and the multiple light emitting elements 80 individually. The multiple circuit boards 70 are housed in the accommodation chamber 11 of the body 10, and the body 10 or/and the case 60 are made of transparent material or translucent material, wherein the control circuit unit 50 is electrically connected with the multiple circuit boards 70 so as to supply the power to the multiple circuit board 70, by which the multiple light emitting elements 80 illuminate lights of various colors, and the lights diffuse to the external environment via the body 10 and the case 60.

The scent air purifier 1 further comprises a scent diffusion unit 12 in which aromatic substances are accommodated, and the scent diffusion unit 12 is housed in the receiving groove 13 of the body 10, the circuit control unit 50 is electrically connected with the power source (not shown) so as to supply the power to the fan 20, by which the fan 20 rotates and delivers the air to flow through the filter element 30 from the external environment, such that the air flows into the receiving groove 13 via the accommodation chamber 11, the fan 20, and the first vents 15 after beings filtered and cleaned by the filter element 30 so that the scent diffusion unit 12 of the receiving groove 13 is blown by the air, thus diffusing scents to the external environment directly via the second through orifice 601 of the case 60. Preferably, the aromatic substances of the scent diffusion unit 12 are any one of essential oil, volatile aromatic liquids, scented oils, scented essences, flower essences, perfumes, and aromatic agent.

As illustrated in FIGS. 2-4, the scent air purifier 1 further comprises a scent carrier 121 being the scent diffusion unit 12, wherein the scent carrier 121 is made of porous solid and is configured to absorb the aromatic substances, wherein the scent carrier 121 is housed in the receiving groove 13 of the body 10 and is blown by the air to as to diffuse fragrance smell out of the scent air purifier 1 via the second through orifice 601 of the case 60.

Accordingly, the scent air purifier 1 diffuses the fragrance smell easily and safely by using the fan 20 and the scent carrier 121.

The scent diffusion unit 12 is a solid capsule which has the scent carrier 121, a shell 122, a lid 124, and multiple second vents 126. The shell 122 has a mouth 1220 defined on a top thereof, the multiple second vents 126 are formed on a bottom of the shell 122. The scent carrier 121 absorbs at least one of the aromatic substances and is housed in the shell 122, and the lid 124 is covered on the mouth 1220, wherein an adjustable spraying gap 128 is defined between the lid 124 and the mouth 1220, the scent diffusion unit 12 (i.e., the solid capsule) is accommodated in the receiving groove 13 of the body 10, and the adjustable spraying gap 128 of the solid capsule extends out of the second through orifice 601 of the case 60. The control circuit unit 50 is electrically connected with the power source (not shown) so as to supply the power to the fan 20, and the fan 20 operates and delivers the air to be filtered by the filter element 30, the air is delivered into the solid capsule through the accommodation chamber 11 of the body 10, the fan 20, the first vent 15, the receiving groove 13, and the multiple second vents 126, hence the air blows the scent carrier 121 so as to diffuse the fragrance smell out of the scent air purifier 1 via the second through orifice 601 of the case 60. Accordingly, the scent air purifier 1 is simplified, reduces power consumption, and operates safely.

As illustrated in FIGS. 2-4, the scent carrier 121 has a third through orifice 1211 defined on a center thereof. The lid 124 has a hollow post 1241 extending outward from a bottom thereof and has female threaded section 1243 formed on a free end of the hollow post 1241. The shell 122 has a male threaded section 1221 extending from a bottom thereof, wherein a diameter of the third through orifice 1211 is more than the hollow post 1241 or the male threaded section 1221. The scent carrier 121 is accommodated in the shell 122, a part of the third through orifice 1211 surrounds the male threaded section 1221, and when the lid 124 is coupled with the shell 122, the hollow post 1241 is inserted into the third through orifice 1211 of the scent carrier 121, and the female threaded section 1243 of the hollow post 1241 is rotatably screwed with the male threaded section 1221 of the shell 122 so as to adjust the adjustable spraying gap 128 between the lid 124 and the shell 122. Alternatively, the female threaded section 1243 of the hollow post 1241 is matingly screwed with the male threaded section 1221 until the adjustable spraying gap 128 between the lid 124 and the mouth 1220 is eliminated, such that the lid 124 covers the mouth 1220 so as to avoid the aromatic substances of the scent carrier 121 contacting with the air of the external environment, thus maintaining the aromatic substances temporarily.

The scent carrier 121 of the scent diffusion unit 12 is made of the porous solid, and the porous solid is any one of plastic, polyethylene (PE), ceramics, plaster, stone, foam, and wood, wherein the scent carrier 121 absorbs the aromatic substances, wherein the aromatic substances are the essential oil or the volatile aromatic liquids, and the volatile aromatic liquids are volatile substances mixed with any one of the essential oil, the scented essences, the flower essences, the perfumes, and the aromatic agent so as to volatilize fragrance molecules, thus producing the fragrance smell. Preferably, the scent carrier 121 absorbs the aromatic substances (such as the essential oil, the scented oils, the scented essences, the flower essences or the perfumes), and the air blows the scent carrier 121 so as to diffuse the fragrance smell out of the scent air purifier 1.

With reference to FIGS. 2 and 4, the scent carrier 121 has multiple apertures 123 extending therethrough and is made of the porous solid so as to absorb the aromatic substances, wherein the multiple apertures 124 pass through the scent carrier 121 and are configured to flow the air. When the aromatic substances or a contact area of the multiple apertures 123 increases, the aromatic substances volatilize easily. In this embodiment, the aromatic substances are any one of the essential oil, the scented essences, and the flower essences.

The shell 122 has multiple locking ribs 1223 separately extending around an inner wall of the shell 22 from a bottom of the shell 122. In this embodiment, the multiple locking ribs 1223 extend beside the multiple second vents 126 respectively. The scent carrier 121 is accommodated in the shell 122, the multiple locking ribs 1223 are configured to engage with the scent carrier 121, wherein a distance is maintained between the bottom of the scent carrier 121 and the shell 122 so that the air flows through the scent carrier 121 and the multiple apertures 123, thus diffusing the aromatic substances effectively.

After running out the aromatic substances of the scent carrier 121, the case 60 is removed so as to supplement the aromatic substances, thus using the cent carrier 121 repeatedly.

The scent carrier 121 is made of the porous solid, and the porous solid is the polyethylene (PE) so as to absorb the aromatic liquids, and the fragrance smell is diffused by the air from the aromatic liquids.

Referring to FIGS. 1-4, the scent air purifier 1 further comprises a button 100 and a housing hole 101, wherein the housing hole 101 is defined between the receiving groove 13 and the accommodation chamber 11, the button 100 is electrically connected with the circuit board 70, the multiple light emitting elements 80, the control circuit unit 50, and the fan 20 so that the control circuit unit 50 sets the multiple light emitting elements 80 to illuminate the lights or the control circuit unit 50 sets the fan 20 to turn on/off or to operate at high or low speeds. The button 100 is housed in the accommodation chamber 11 and an upper end of the button 100 extends into the bottom of the receiving groove 13 so as to contact with the bottom of the scent diffusion unit 12 (such as the solid capsule or the scent carrier 121). Accordingly, the scent diffusion unit 12 is pressed so as to drive the button 100, and the fan 20 or/and the multiple light emitting elements 80 are turned on/off by the button 100 easily.

The button 100 further includes a cap 108 fitted thereon so as to protect the button 100, when the bottom of the scent diffusion unit 12 (such as the solid capsule or the scent carrier 121) presses the button 100.

As shown in FIGS. 2-4, the scent air purifier 1 further comprises a positioning disc 105, a pushing disc 107, and a resilient element 109. The positioning disc 105 has a pore 1051 and is located between the holder 40 and the filter element 30. The pushing disc 107 is mounted below the pore 1051, and an upper end of the pushing disc 107 extends out of the pore 1051 and abuts against the bottom of the filter element 30, wherein a first side of the resilient element 109 contacts against a bottom of the holder 40, and a second side of the resilient element 109 pushes the pushing disc 107 to abut against the filter element 30 securely.

As shown in FIGS. 2-4, the scent air purifier 1 further comprises a stopping disc 102 and a flexible ring 104, wherein the stopping disc 102 has a fourth through orifice 1021, and the stopping disc 102 is connected with a bottom of the fan 20. A first side of the flexible ring 104 abuts against the stopping disc 102, and a second side of the flexible ring 104 contacts with the mouth 1220 of the filter element 30, such that the flexible ring 104 abuts against the stopping disc 102 so as to absorb vibration and noises from the fan 20.

As illustrated in FIGS. 2-4, the scent air purifier 1 further comprises a detector 106 electrically connected with the control circuit unit 50 and the fan 20 and configured to detect polluted air. For example, when the detector 106 senses the particulate matters and the dusts in the polluted air, the detector 106 sends a signal to the control circuit unit 50 so that the control circuit unit 50 indicates the fan 20 to operate at the high speed, and the fan 20 delivers the air to flow through the filter element 30, thus filtering the air efficiently.

Preferably, the filter element includes a first filtration layer, a second filtration layer, and a third filtration layer. The first filtration layer is made of nanosilver so as to stop hairs, furs, dusts, debrides, and fluffs. The second layer is high-efficiency particulate air (HEPA) so as to attach dusts and PM 2.5. The third layer is an activated carbon filter so as to filter odors, smoke, and formaldehyde.

While the preferred embodiments of the invention have been set forth for the purpose of disclosure, modifications of the disclosed embodiments of the invention as well as other embodiments thereof may occur to those skilled in the art. The scope of the claims should not be limited by the preferred embodiments set forth in the examples, but should be given the broadest interpretation consistent with the description as a whole.

What is claimed is:

1. A scent air purifier comprising:
    a body including an accommodation chamber, a receiving groove, a first vent, wherein the accommodation chamber is defined in the body, the receiving groove is located above the accommodation chamber, and the first vent is formed between and communicates with the accommodation chamber and the receiving groove;
    a fan accommodated in the accommodation chamber;
    a filter element connected below the accommodation chamber of the body and communicating with air from an external environment outside the body so that the fan delivers the air to flow through the first vent and the receiving groove, after the fan draws the air from the external environment;
    a holder is connected with a lower end of the body;
    a circuit control unit housed in the holder and electrically connected with a power source and the fan; and
    a case, a support loop, and multiple tabs, wherein the case includes a second through orifice formed on a side of the case, and the multiple tabs are arranged around a peripheral side of the support loop, wherein the case is hollow, the support loop is fitted on an outer wall of the body, when the case covers on the outer wall of the body, an inner wall of the case is detachably retained with the multiple tabs of the support loop.

2. The scent air purifier as claimed in claim 1, wherein the body further includes a first through orifice defined between an upper end of the accommodation camber and the receiving groove and communicating with the accommodation chamber.

3. The scent air purifier as claimed in claim 1 further comprising multiple clean meshes arranged around an outer wall of the filter element; multiple fixing elements, and each of the multiple cleaning meshes including a housing trench defined inside an outer wall of each cleaning mesh and accommodating the multiple fixing elements, wherein two ends of each of the multiple fixing elements fix the filter element.

4. The scent air purifier as claimed in claim 1 further comprising multiple circuit boards and multiple light emitting elements respectively arranged on the multiple circuit boards, wherein the multiple circuit boards are electrically connected with the control circuit unit and the multiple light emitting elements individually; the multiple circuit boards are housed in the accommodation chamber of the body, and the body or/and the case are made of transparent material or translucent material.

5. The scent air purifier as claimed in claim 1 further comprising a scent diffusion unit in which aromatic substances are accommodated, and the scent diffusion unit is housed in the receiving groove of the body.

6. The scent air purifier as claimed in claim 5, wherein the scent diffusion unit is a scent carrier made of porous solid and configured to absorb the aromatic substances.

7. The scent air purifier as claimed in claim 6, wherein the scent diffusion unit is a solid capsule which has the scent carrier, a shell, a lid, and multiple second vents; the shell has a mouth defined on a top thereof, the multiple second vents are formed on a bottom of the shell, the scent carrier absorbs at least one of the aromatic substances and is housed in the shell, and the lid is covered on the mouth, wherein an adjustable spraying gap is defined between the lid and the mouth.

8. The scent air purifier as claimed in claim 7, wherein the scent carrier has a third through orifice defined on a center thereof; the lid has a hollow post extending outward from a bottom thereof and has female threaded section formed on a free end of the hollow post; the shell has a male threaded section extending from the bottom thereof, wherein a diameter of the third through orifice is more than the hollow post or the male threaded section, the scent carrier is accommodated in the shell, a part of the third through orifice surrounds the male threaded section, and when the lid is coupled with the shell, the hollow post is inserted into the third through orifice of the scent carrier, and the female threaded section of the hollow post is rotatably screwed with the male threaded section of the shell so as to adjust the adjustable spraying gap between the lid and the shell.

9. The scent air purifier as claimed in claim 8, wherein the scent carrier of the scent diffusion unit is made of the porous solid, and the porous solid is any one of plastic, polyethylene (PE), ceramics, plaster, stone, foam, and wood.

10. The scent air purifier as claimed in claim 9, wherein the scent carrier has multiple apertures extending therethrough.

11. The scent air purifier as claimed in claim 5 further comprising a button and a housing hole, wherein the housing hole is defined between the receiving groove and the accommodation chamber of the body, the button is electrically connected with the circuit board, the multiple light emitting elements, the control circuit unit, and the fan, wherein an upper end of the button extends into a bottom of the receiving groove so as to contact with a bottom of the scent diffusion unit.

12. The scent air purifier as claimed in claim 1 further comprising a positioning disc, a pushing disc, and a resilient element, wherein the positioning disc has a pore and is located between the holder and the filter element, the pushing disc is mounted below the pore, and an upper end of the pushing disc extends out of the pore and abuts against a bottom of the filter element, wherein a first side of the resilient element contacts against a bottom of the holder, and a second side of the resilient element pushes the pushing disc.

13. The scent air purifier as claimed in claim 1 further comprising a stopping disc and a flexible ring, wherein the stopping disc has a fourth through orifice, and the stopping disc is connected with a bottom of the fan, wherein a first side of the flexible ring abuts against the stopping disc, and a second side of the flexible ring contacts with the mouth of the filter element.

14. The scent air purifier as claimed in claim 1 further comprising a detector electrically connected with the control circuit unit and the fan.

15. A scent air purifier comprising a scent diffusion unit, wherein the scent diffusion unit is a solid capsule which has a scent carrier, a shell, a lid, and multiple second vents; the shell has a mouth defined on a top thereof, the multiple second vents are formed on a bottom of the shell, the scent carrier absorbs at least one of the aromatic substances and is housed in the shell, and the lid is covered on the mouth, wherein an adjustable spraying gap is defined between the lid and the mouth, wherein the scent carrier has a through orifice defined on a center thereof; the lid has a hollow post extending outward from a bottom thereof and has female threaded section formed on a free end of the hollow post; the shell has a male threaded section extending from the bottom thereof, wherein a diameter of the through orifice is more than the hollow post or the male threaded section, the scent carrier is accommodated in the shell, a part of the through orifice surrounds the male threaded section, and when the lid is coupled with the shell, the hollow post is inserted into the through orifice of the scent carrier, and the female threaded section of the hollow post is rotatably screwed with the male threaded section of the shell so as to adjust the adjustable spraying gap between the lid and the shell.

16. The scent air purifier as claimed in claim 15, wherein the scent carrier of the scent diffusion unit is made of the porous solid, and the porous solid is any one of plastic, polyethylene (PE), ceramics, plaster, stone, foam, and wood.

17. The scent air purifier as claimed in claim 16, wherein the scent carrier has multiple apertures extending therethrough.

18. The scent air purifier as claimed in claim 17, wherein the shell has multiple locking ribs separately extending around an inner wall of the shell from the bottom of the shell.

* * * * *